United States Patent [19]

Bluthe et al.

[11] Patent Number: 4,990,657

[45] Date of Patent: Feb. 5, 1991

[54] PROCESS FOR THE PREPARATION OF AROMATIC ACID

[75] Inventors: Norbert Bluthe, Villeurbanne; Robert Perron, Charly, both of France

[73] Assignee: Rhone Poulenc Chimie, Courbevoie, France

[21] Appl. No.: 355,852

[22] Filed: May 19, 1989

Related U.S. Application Data

[63] Continuation of Ser. No. 78,115, Jul. 27, 1987, abandoned.

[30] Foreign Application Priority Data

Jul. 25, 1986 [FR] France ............................ 86 10991
Jul. 25, 1986 [FR] France ............................ 86 10992
Jul. 25, 1986 [FR] France ............................ 86 10993

[51] Int. Cl.$^5$ ......................................... C07C 51/10
[52] U.S. Cl. ........................... 562/406; 549/436; 558/353; 560/97
[58] Field of Search ................ 562/406; 549/436; 558/353; 560/97

[56] References Cited

U.S. PATENT DOCUMENTS 3,988,358 10/1976 Heck ................................. 560/97
4,034,004 7/1977 Cassar et al. ..................... 260/515
4,374,262 2/1983 McGinnis ........................... 562/406
4,654,436 3/1987 Lane .................................. 562/406
4,668,816 5/1987 Epstein ............................. 562/406
4,820,823 4/1989 Tanaka .............................. 562/406

FOREIGN PATENT DOCUMENTS 034292 8/1981 European Pat. Off. .
3605882 8/1986 Fed. Rep. of Germany ...... 562/406

OTHER PUBLICATIONS

Schoenberg, J. Org. Chem., 39, pp. 3318–3326.
Stille, J. Org. Chem., 40 pp. 532–534 (1975).

Primary Examiner—Michael L. Shippen
Attorney, Agent, or Firm—Finnegan, Henderson, Farabow, Garrett, and Dunner

[57] ABSTRACT

A process for the preparation of an aromatic acid comprising the step of combining an aromatic halide having at least one iodine or bromine substituent with:
 a. a water-immiscible organic solvent,
 b. a palladium-based catalyst,
 c. a palladium-complexing agent,
 d. a tertiary nitrogen-containing organic base,
 e. water and
 f. carbon monoxide.

The process is performed in a two-phase liquid medium and in the substantial absence of a phase transfer agent.

17 Claims, No Drawings

PROCESS FOR THE PREPARATION OF AROMATIC ACID

This application is a continuation of application Ser. No. 07/078,115, filed July 27, 1987 abandoned.

BACKGROUND

1. Field of the Invention

The present invention relates to a new process for the preparation of aromatic acids. More particularly, the invention relates to an two-phase improved process for the production of aromatic acids by hydrocarbonylation of aromatic halides in the presence of a water-immiscible organic solvent, a palladium-based catalyst, a tertiary nitrogen-containing organic base, water and carbon monoxide.

2. Background of the Invention

Two recent patents may be considered among the various known methods of preparing aromatic acids. U.S. Pat. No. 4,034,004 issued July 5, 1977 ("the '004 patent") discloses a process for the preparation of carboxylic acids by the reaction of aromatic or aliphatic organic halides with carbon monoxide in an alkaline medium using phosphinic palladium complexes as catalysts. The reaction takes place in a two-phase medium in the presence of a quaternary alkylammonium salt as a phase transfer agent, with the aqueous phase containing an inorganic alkaline base and the quaternary ammonium salt.

The '004 patent states that the disclosed reaction should take place at a temperature of between 50° and 150° C. However, above this temperature, and even above 120° C., carbon monoxide reacts with the alkaline base to produce sodium formate. The formation of this unwanted by-product needlessly uses up the alkaline base and the carbon monoxide which has been introduced into the reaction mixture, thus greatly reducing the space time yield of the process. As used herein, the term "space time yield" means the quantity of aromatic acid produced per unit (e.g., hour) of reaction time and per unit (e.g., liter) of liquid reaction mixture.

Further, Example 2 of the '004 patent demonstrates the inefficiencies encountered when one attempts to recycle the phosphine-complexed palladium catalyst using the disclosed process. During the first recycle, the yield of aromatic acid produced is about 10% less than the yield of the initial reaction using fresh catalyst. Therefore, the process of the '004 patent cannot be extrapolated to more than 4 or 5 successive recycles due to these increasingly poorer yields.

Patent EP 34,292 reveals a process for the preparation of anthranilic acid by combining carbon monoxide, water, a trialkylamine, a catalyst based on palladium complexed with a phosphine, and an acylamino-, iodo- or bromobenzene.

However, the quantity of water employed is so low that a two-phase system is not produced. Rather, the reaction of this patent takes place in a single, highly viscous homogeneous phase. As a result, the process of EP 34,292 does not permit easy separation of the reaction product from the catalyst and does not allow the catalyst to be readily recycled. Therefore, while the disclosed process is suitable for producing pharmaceutical products or chemical intermediates having a high unit value which are produced in relatively small amounts, it is not well-adapted for products which are produced on an industrial scale for large-volume use.

In contrast, the present invention provides improved processes which can be exploited economically on a large, industrial scale.

SUMMARY OF THE INVENTION

In accordance with the present invention, a process for the preparation of an aromatic acid comprises the step of combining an aromatic halide having at least one iodine or bromine substituent with:

a. a water-immiscible organic solvent,
b. a palladium-based catalyst,
c. a palladium-complexing agent,
d. a tertiary nitrogen-containing organic base,
e. water and
f. carbon monoxide, wherein the process is performed in a two-phase liquid medium and in the substantial absence of a phase transfer agent. The palladium-complexing agent may be present either in the form of a complex, such as a complex with the palladium-based catalyst, or in a free, uncomplexed state.

DETAILED DESCRIPTION OF THE INVENTION

The chemical reaction employed in the process of the present invention may be summarized as follows:

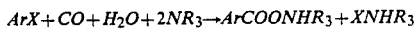

$$ArX + CO + H_2O + 2NR_3 \rightarrow ArCOONHR_3 + XNHR_3$$

The aromatic halide of the present invention can be any aromatic halide having at least one iodine or bromine substituent. Preferably, the aromatic halide has the following formula (I):

$$(X)_n-Ar-(R_1)_{n1} \qquad (I)$$

wherein

X denotes bromine or iodine,

Ar denotes a mono- or polycylic or heterocyclic radical, n is equal to 1 or 2 per ring, $n_1$ is an integer greater than or equal to 1 and smaller than or equal to 4, and $R_1$ denotes one or more identical or different radicals selected from the group consisting of hydrogen, fluoro, chloro, cyano, alkyl, alkenylene, alkoxy, cycloalkyl, cycloalkoxy, alkylcarbonyloxy, cycloalkylcarbonyloxy, aryl, aryloxy, arylcarbonyloxy and aryloxycarbonyl, wherein the alkyl and aryl moieties each contain from 1 to 20 carbon atoms and may be unsubstituted or substituted with at least one halogen selected from the group consisting of fluorine and chlorine.

In formula (I), Ar may be a mono- or polycyclic or heterocyclic radical. Preferred polycyclic radicals include condensed rings such as naphthalene and anthracene; rings linked together by a covalent bond such as biphenyl; or rings linked together by a hetero atom, for example, by oxygen or sulfur, such as diphenyl oxide. Preferably, Ar is either a benzene moiety or a diphenyl ether moiety.

In preferred compounds of formula (i), $R_1$ denotes:

a. an alkyl or alkoxy group containing 1 to 4 carbon atoms such as methyl, ethyl, propyl, isopropyl, butyl, isobutyl, trifluoromethyl, difluorochloromethyl, methoxy, ethoxy, propoxy, butoxy, trifluoromethoxy or trichloromethoxy;

b. a cycloalkyl or cycloalkoxy group containing 5 to 10 carbon atoms such as cyclopentyl, cyclohexyl or cyclooctyl;

c. an aryl or aryloxy group such as phenyl, xylyl, toluyl, methoxyphenyl, ethoxyphenyl, phenoxy, methylphenoxy or dimethylphenoxy;

d. an alkoxycarbonyl or alkylcarbonyloxy group in which the alkyl group preferably has 1 to 4 carbon atoms; or e. a cycloalkoxycarbonyl or cycloalkylcarbonyloxy group such as cyclopentyloxycarbonyl or cyclohexyloxycarbonyl.

Examples of useful aromatic halides of formula (I) include bromobenzenes, bromotoluenes, dimethylbromobenzenes, fluorobromobenzenes, fluoroiodobenzenes, difluorobromobenzenes, trifluoromethylbromobenzenes, trifluoromethyliodobenzenes, difluorochloromethylbromobenzenes, difluorochloromethoxybromobenzenes, bromobenzonitriles, dibromobenzenes, diiodobenzenes, bromonaphthalenes, bromopyridines, bromodiphenyl ethers, methyl bromobenzoates, bromoanisoles, bromophenetoles, dimethoxybromobenzenes, 3,4,5-trimethoxybromobenzenes, 3-bromomethylenedioxybenzenes, bromodiphenyl ethers and dibromodiphenyl ethers.

Particularly preferred aromatic halides are p-bromodiphenyl ether and di(4-bromophenyl) ether.

The aromatic halide of the invention is combined with at least one water-immiscible organic solvent which is inert under the reaction conditions of the process. Useful water-immiscible organic solvents include saturated aliphatic or alicyclic hydrocarbons such as hexane and cyclohexane; aromatic hydrocarbons such as benzene, toluene and xylene; haloaromatic hydrocarbons such as chlorobenzene; alkyl esters such as methyl adipate; benzyl esters such as methyl benzoate; aryl esters such as methyl terephthalate and aromatic ethers such as diphenyl ether.

Among these water-immiscible organic solvents, chlorobenzene and diphenyl ether are preferred. Diphenyl ether is particularly preferred when the process of the invention is being used to prepare phenoxybenzoic acid.

Use of either chlorobenzene or diphenyl ether as a solvent for the aromatic halide has at least two advantages when compared with solvents which are widely employed in carbonylation reactions in the prior art, for example, alkylbenzene solvents such as toluene. First, the use of these solvents increases the space time yield for the reaction. Further, these solvents improve the stability of the palladium-based catalyst, thus making possible the reduction of the quantity of palladium-complexing agent necessary to keep the palladium-based catalyst soluble and in recyclable form.

The palladium-based catalyst which is used in the invention can comprise metallic palladium, the palladium salt of an inorganic or organic acid, or a complex formed by palladium with a palladium-complexing agent.

Specific examples of palladium salts of inorganic or organic acids include palladium (II) carboxylates such as acetates, propionates, butyrates or benzoates.

Specific examples of complexes of palladium with palladium-complexing agents include complexes of the general formulae PdX$_2$[P(R)$_3$]$_2$ or PdX$_2$[P(OR)$_3$]$_2$, in which X denotes a halogen atom, such as bromine or chlorine, or an inorganic or carboxylic acid residue, and R denotes a hydrocarbon radical. Preferred palladium complexes include dichlorobis(triphenylphosphino)palladium (II) and dichlorobis(tritolylphosphino)palladium (II).

The palladium-complexing agent used in the invention can be any compound which donates electron pairs to palladium, such as a phosphine, a phosphite or an arsine compound. Examples of particularly useful palladium-complexing agents include, without any limitation being implied, triphenylphosphine, triphenyl phosphite, diethylphenylphosphine, diethylphenyl phosphite, tritolylphosphine, tritolyl phosphite, trinaphthylphosphine, trinaphthyl phosphite, diphenylmethylphosphine, diphenylmethyl phosphite, diphenylbutylphosphine, diphenylbutyl phosphite, tri(p-methoxycarbonylphenyl)phosphine, tri(p-methoxycarbonylphenyl) phosphite, tri(p-cyanophenyl)phosphine, tri(cyanophenyl) phosphite, triethyl phosphite, tributylphosphine and tributyl phosphite.

The quantity of palladium-based catalyst may vary within wide limits. Typically, the quantity of the catalyst varies between about $10^{-5}$ and $10^{-1}$ gram-atoms of metallic palladium (or moles of palladium salt or palladium complex) per mole of aromatic halide, and preferably varies between $10^{-4}$ and $10^{-2}$ gram-atoms (or moles) per mole.

Depending on the nature of the catalyst and/or on the reaction conditions, the palladium-complexing agent is not necessarily required in the reaction medium in a free, uncomplexed form. When the catalyst consists of a complex formed by palladium with a complexing agent, the presence of excess complexing agent in a free state is not essential. However, the presence of free complexing agent may be advantageous when the reaction is carried out at elevated temperature, for example, at a temperature above 150° C. Further, when the catalyst is metallic palladium which is not complexed or a palladium salt, such as a palladium carboxylate, the process must be carried out in the presence of free complexing agent. Thus, as used herein, reference to the presence of, or combinations containing, a palladium-complexing agent includes either free, uncomplexed palladium-complexing agent or complexing agent in the form of a complex, such as a complex with the palladium-based catalyst.

When the reaction of the invention is conducted in the presence of a palladium-complexing agent containing phosphorus, the ratio of the total number of gram-atoms of phosphorus (including both complex and free forms) (P) to the number of gram-atoms of metal (M) is at least equal to 2. However, the ratio P/M can assume values as high as 10,000. In general, a ratio P/M of between 5 and 1,000 is suitable.

The tertiary nitrogen-containing organic base of the invention can be any tertiary nitrogen-containing organic base which is capable of neutralizing the aromatic acid formed and the hydracid released during the reaction. Tertiary heterocyclic bases such as pyridine and pocolines can be employed. Also useful are amines of the general formula:

$N-(R_1)_3$ in which the $R_1$ groups, which can be identical or different, denote hydrocarbon residues containing from 1 to 20 carbon atoms, such as alkyl, cycloalkyl or aryl groups. Preferably, $R_1$ denotes an alkyl group containing from 1 to 10 carbon atoms or a cycloalkyl group containing from 5 to 10 carbon atoms. Examples of such bases include triethylamine, tri-n-propylamine, tri-n- butylamine, methyldibutylamine, methyldicyclohexylamine and ethyl diisopropylamine. Triethylamine is a particularly preferred tertiary nitrogen-containing organic base.

The quantity of the tertiary nitrogen-containing organic base should be sufficient to neutralize the aromatic acid formed and the hydracid released by the reaction. In other words, at least two moles of this base are required for each equivalent of reactive halogen (bromine and/or iodine) in the aromatic halide molecule. There is no upper limit to the quantity of base which may be added. A quantity of organic base suitable to promote the economy of the process can be readily determined by one of ordinary skill in the art.

The process of the present invention is conducted in a two-phase liquid medium with the organic medium containing the aromatic halide, which is preferably dissolved in a water-immiscible organic solvent; the palladium-based catalyst with a palladium-complexing agent if appropriate; and the nitrogen-containing organic base.

A sufficient amount of water must also be present to form a second, aqueous phase and to ensure the solubility of both the salts of the aromatic acid produced during the process and of the hydracid released with the tertiary nitrogen-containing organic base. This minimum quantity of water will largely be determined by the aromatic acid formed. For example, in the case of the preparation of para-phenoxybenzoic acid from bromodiphenyl ether by the process of the invention, it is preferred to employ a minimum of about 0.29 liters of water per mole of bromodiphenyl ether, i.e., a maximum of 3.5 moles of bromodiphenyl ether is typically used per liter of water.

The temperature at which the process of the invention may be carried out can vary within wide limits. It is preferred, however, to maintain the reaction temperature between 50° and 250° C. and, more preferably, between 100° and 200° C.

The total reaction pressure of the present process can vary with the temperature and the materials employed within wide limits, but should be adapted to maintain the desired partial pressure of carbon monoxide. Adapting the total reaction pressure in this way to control the partial pressure of carbon monoxide can be easily done by one of ordinary skill in the art.

The partial pressure of monoxide can also vary widely but, preferably, is maintained at a level not higher than 5 bars. Still more preferably, the partial pressure of carbon monoxide does not exceed 3 bars.

The acceleration of a reaction between a gas and a liquid by increasing the pressure of the gas is an established presumption in chemistry. Since carbon monoxide is one of the reactants in the reaction of the invention, one skilled in the art would expect that an increase in pressure would accelerate the reaction and that a decrease in pressure would slow the reaction down. Nevertheless, in contrast to what one of ordinary skill in the art would expect, reducing the carbon monoxide pressure during the reaction actually improves the space time yield of the process of the invention rather than decreasing it.

The process of the invention is performed in the substantial absence of a phase transfer agent, such as quaternary alkyl ammonium salts.

From a practical standpoint, the process according to the invention can be implemented by introducing the aromatic halide, the water-immiscible organic solvent, the palladium-based catalyst, the optional free palladium-complexing agent, the tertiary nitrogen-containing organic base and water into an autoclave; closing the autoclave; and providing a suitable pressure of carbon monoxide. The contents of the autoclave are typically heated, with stirring, to maintain a suitable temperature until gas absorption ceases. When the reaction is finished, the contents of the autoclave can be cooled, the autoclave purged of gas, and the aqueous phase containing the aromatic acid (which is neutralized by the tertiary nitrogen-containing organic base) is separated off. After treatment with an inorganic acid, the free acid can be isolated from the aqueous phase by precipitation, extraction with fresh amounts of a water-immiscible solvent, or any other conventional method known in the art for this purpose.

The process according to the invention may be carried out either continuously or noncontinuously.

The aromatic acids produced using the process of the present invention correspond to the starting aromatic halides with the iodine or bromine substituent of the halide replaced with a —COOH group. Typically, these aromatic acids correspond to the general formula (II):

$$(R_1)_{n_1}\text{-Ar-}(COOH)_n \qquad (II)$$

in which Ar, n, $n_1$ and $R_1$ have the same meaning as in formula (I) described above.

Exemplary monoacids include benzoic, chlorobenzoic, toluic, methoxybenzoic, trifluoromethoxybenzoic, trifluoromethylbenzoic and phenoxybenzoic acids. Exemplary diacids include phthalic acids and di(4-carboxyphenyl) ethers.

The following examples further illustrate preferred embodiments of the present invention and show how the invention can be implemented in practice. The examples should in no way be considered limiting, but are merely illustrative of the various features of the present invention.

EXAMPLE 1

The following materials were charged into a pressure-resistant reactor made of stainless steel (trade name Hastelloy® B2) which has been equipped with a heating device and stirred with a stirrer of the Cavitator type:

37.35 g of para-bromophenoxybenzene (150 mmol),
67.2 mg of palladium diacetate (0.3 mmol),
2.36 g of triphenylphosphine (9 mmol),
33.33 g of triethylamine (330 mmol),
45 ml of water and
30 ml of toluene.

The reactor was purged with carbon monoxide and the temperature was gradually raised to 130° C. At 100° C., carbon monoxide was introduced to give a total reactor pressure of 6 bar at 130° C. The reactor was connected to a carbon monoxide reserve to keep the pressure constant, and the progress of the reaction was followed by means of the pressure drop of this reserve. The initial absorption rate ("$V_i$") was 150 mmol h$^{-1}$.

After 1 hour and 45 minutes of reaction time, the absorption of carbon monoxide ceased. The reactor was cooled, the aqueous phase was allowed to separate, and then drained off.

The same quantities of para-bromophenoxybenzene, triethylamine and water given above were then again charged into the reactor for recycling. The process was repeated four times in this manner. The results are collated in the table which follows:

| Recycle | ΔP (bar) | Reaction time | $V_i$ (mmol h$^{-1}$) |
| --- | --- | --- | --- |
| 1 | 22 | 1 h 45 min | 155 |
| 2 | 23 | 1 h 30 min | 197 |
| 3 | 24 | 1 h 15 min | 218 |
| 4 | 22 | 1 h 30 min | 197 |

These tests showed that it was possible to recycle the catalyst while maintaining its activity. The two-phase liquid medium system employed made it possible to drain off the reaction product present in the aqueous phase under carbon monoxide pressure, while the catalyst system was kept in the reactor in the organic phase for recycling.

EXAMPLE 2

The same procedure as in Example 1 was again followed, but the initial reaction was deliberately limited to an incomplete conversion (below, "conv.").

| Test | ΔP (bar) | Reaction time | $V_i$ (mmol h$^{-1}$) |
| --- | --- | --- | --- |
| Initial test Conv. approx. 80% | 17 | 50 min | 170 |
| 1st recycle | 22 | 1 h | 194 |
| 2nd recycle | 23 | 55 min | 197 |
| 3rd recycle | 23 | 1 h | 203 |
| 4th recycle | 23.5 | 55 min | 200 |
| 5th recycle | 23 | 50 min | 256 |
| 6th recycle | 24 | 45 min | 280 |

This series of tests showed that the catalyst could be recycled at least six (6) times while retaining its initial activity. After the fourth recycle, there was even a 25% gain in activity.

EXAMPLE 3

The following materials:
12.45 g of para-bromophenoxybenzene (50 mmol),
22.4 mg of palladium diacetate (0.1 mmol),
524 mg of triphenylphosphine (2 mmol) and
11.11 g of triethylamine (110 mmol)
were charged into a 125-ml Hastelloy® autoclave. 10 ml of toluene and 15 ml of water were added.

The reactor was then closed, purged with carbon monoxide, and stirred by means of a reciprocating system. The temperature was gradually raised to 130° C., and carbon monoxide was introduced into the reactor at 100° C. so as to produce a total pressure of 6 bar at 130° C. The reactor was connected to a carbon monoxide reserve, which kept the pressure in the reactor constant and which was used to determine the absorption of carbon monoxide by measuring the pressure drop.

After 2 hours and 20 minutes of reaction time, the absorption of carbon monoxide ceased. The reactor was cooled and purged of gas. The organic phase and the aqueous phase were then separated. The aqueous phase was acidified with 2N HCl to pH=2. The precipitated acid was filtered off, washed and dried. 10.34 g of para-phenoxybenzoic acid was obtained (97% yield). The space time yield for the acid product was 89 g/hour/liter.

Further, when the reaction was finished, 84% of the palladium charged in theory was recovered in the organic phase.

EXAMPLES 4 to 6

The same procedure as in Example 3 was repeated with the modifications given in the following table, along with the results obtained in each test.

| Example | Solvent | PPh$_3$ (mmol) | Reaction time | Space time yield (g/h/l) | Palladium (%) |
| --- | --- | --- | --- | --- | --- |
| 4 | PhCl | 2 | 1 h 50 min | 115 | 100 |
| 5 | PhOPh | 2 | 2 h | 100 | 73 |
| 6 | toluene | 4 | 5 h | 40 | 100 |

Chlorobenzene gave a gain in space time yield. Further, compared with the other solvents, a smaller quantity of phosphine was required to keep the catalyst in solution for recycling.

EXAMPLE 7

The following materials:
224 mg of palladium diacetate (1 mmol),
1.31 g of triphenylphosphine (5 mmol),
11.11 g of triethylamine (110 mmol) and
12.45 g of para-bromophenoxybenzene (0.05 mol) were charged into a 125-ml Hastelloy® B2 autoclave. 20 ml of toluene and 20 ml of water were added. The autoclave was closed and then purged with carbon monoxide. The temperature was raised to 130° C. while the autoclave was stirred by means of a reciprocating system. At 100° C., carbon monoxide was introduced so as to produce a total pressure of 7 bar at 130° C. The partial pressure of carbon monoxide was approximately 4 bar.

Throughout the reaction period, the reactor was connected to a carbon monoxide reserve, which kept the reaction pressure constant. The progress of the reaction was followed by the pressure drop in the reserve. The initial absorption rate, measured by the pressure drop in the reserve, was 56 bar h$^{-1}$.

After 30 minutes of reaction time, the starting material was completely used up. The yield of para-phenoxybenzoic acid was quantitative. The space time yield was 340 g/hour/liter.

EXAMPLE 8

(Comparative Example)

The same procedure as in Example 1 was followed, but the pressure in the reactor at 130° C. was maintained at 30 bar. The partial pressure of carbon monoxide was 27 bar. The initial absorption rate was 14 bar h$^{-1}$.

Absorption of carbon monoxide ceased after 3 hours of reaction time. The space time yield was 60 g/hour/liter.

This example showed that it was preferable to work at a low partial pressure of carbon monoxide.

EXAMPLE 9

The same procedure as in Example 1 was followed, but 22.4 mg of palladium diacetate (0.1 mmol) and 1.05 g of triphenylphosphine were charged into the reactor. The maximum absorption rate was 6.4 bar h$^{-1}$.

The absorption of carbon monoxide stopped after 5 hours. The yield of para-phenoxybenzoic acid was quantitative. The space time yield was 34 g/hour/liter.

EXAMPLE 10

The same procedure as in Example 3 was followed, but at a temperature of 150° C. The partial pressure of carbon monoxide was 3 bar. The initial absorption rate was 16.3 bar h$^{-1}$.

After 50 minutes of reaction time, the starting material was completely converted. The space time yield was 200 g/hour/liter.

EXAMPLE 11 (Comparative Example for Example 3)

The following materials:
22.4 mg of palladium diacetate (0.1 mmol),
524 mg of triphenylphosphine,
11.11 g of triethylamine (110 mmol) and
12.45 g of para-bromophenoxybenzene (0.05 mol) were charged into a 125-ml Hastelloy ® B2 autoclave. The reaction procedure was similar to that of Example 1 except that the total pressure was maintained at 4 bar throughout the test. The partial pressure of carbon monoxide was 1 bar. The initial absorption rate was 6 bar h$^{-1}$.

After 4 hours, no further absorption of carbon monoxide took place. When the reaction was finished, the two phases, aqueous and organic, were poured out and separated. The aqueous phase was acidified with 2N HCl to pH=2. The para-phenoxybenzoic acid precipitated in this manner was filtered off, washed and dried. 10.59 g (99% yield) of a product whose purity was at least 98% was obtained. The space time yield was 40 g/hour/liter.

When compared with the results of Example 3, this test showed that the partial pressure of carbon monoxide could be less than 1 bar without lowering the space time yield to an unacceptably low level.

EXAMPLE 12

The same procedure as in Example 4 was followed, but 11.2 mg of palladium diacetate (0.05 mmol), 10 ml of toluene and 15 ml of water were used.

After 2 hours and 10 minutes of reaction, the absorption of carbon monoxide ceased, and the yield of para-phenoxybenzoic acid was quantitative. The space time yield was 100 g/hour/liter.

EXAMPLE 13

The following materials:
112 mg of palladium diacetate (0.5 mmol),
524 mg of triphenylphosphine (2 mmol),
18.5 g of tributylamine (100 mmol) and
6.2 g of di(4-bromophenyl) ether (25 mmol) were charged into a 125-ml Hastelloy ® B2 reactor. 10 ml of chlorobenzene and 15 ml of water were then added. The procedure was similar to that followed in the above examples.

After 2 hours and 30 minutes of reaction time at a total pressure of 10 bar and 130° C., the absorption of carbon monoxide ceased. After the reactor was cooled and purged free of gas, the aqueous phase was separated from the organic phase. The aqueous phase was acidifed with 2N HCl to pH=2. The precipitated diacid was filtered off, washed and dried. 4.53 g of product (73% yield) were obtained. The space time yield was 36 g/hour/liter.

We claim:

1. A process for the preparation of an aromatic acid comprising the step of combining an aromatic halide having at least one iodine or bromine substituent bonded directly to the aromatic ring system with:
   a. a water-immiscible organic solvent,
   b. a palladium-based catalyst,
   c. a phosphine or a phosphite palladium-complexing agent,
   d. a tertiary nitrogen-containing organic base,
   e. water and
   f. carbon monoxide, wherein the process is performed in a two-phase liquid medium and in the substantial absence of a phase transfer agent to produce said aromatic acid wherein a —COOH group is bonded directly to the aromatic ring system and wherein the partial pressure of carbon monoxide is not higher than 5 bars.

2. The process of claim 1 wherein the aromatic halide corresponds to the formula (I):

$(X)_n\text{-Ar-}(R_1)_{n1}$      (I)

in which:
X denotes bromine or iodine,
Ar denotes a mono- or polycylic or heterocyclic aromatic radical,
n is equal to 1 or 2 per ring,
n$_1$ is an integer greater than or equal to 1 and smaller than or equal to 4, and
Rhd 1 denotes one or more identical or different groups selected from the group consisting of hydrogen, fluoro, chloro, cyano, alkyl, alkenylene, alkoxy, cycloalkyl, cycloalkoxy, alkylcarbonyloxy, cycloalkylcarbonyloxy, aryl, aryloxy, arylcarbonyloxy and aryloxycarbonyl, wherein the alkyl moiety contains from 1 to 20 carbon atoms and wherein the alkyl and aryl moieties may each be unsubstituted or substituted with one or more fluorine and/or chlorine atoms.

3. The process of claim 2 wherein Ar in formula (I) denotes a benzene moiety or a diphenyl ether moiety.

4. The process of claim 1 where the aromatic halide is para-bromophenyl ether or di(4-bromophenyl) ether.

5. The process of claim 1 wherein the water-immiscible organic solvent is selected from the group consisting of aliphatic, alicyclic, aromatic and haloaromatic hydrocarbons; alkyl esters; methyl benzoate; aromatic ethers; and aryl esters selected from the group consisting of methyl terephthalate and dibutyl phthlate.

6. The process of claim 5 wherein the water-immiscible organic solvent is chlorobenzene or diphenyl ether.

7. The process of claim 5 wherein the water-immiscible organic solvent is chlorobenzene.

8. The process of claim 1 wherein the palladium-based catalyst comprises metallic palladium, the palladium salt of an inorganic or organic acid, or a complex formed by palladium and a palladium-complexing agent.

9. The process of claim 1 wherein the quantity of the palladium-based catalyst ranges from 10$^{-5}$ to 10$^{-1}$ gram-atoms of metallic palladium (or moles of palladium salt or palladium complex) per mole or aromatic halide.

10. The process of claim 1 wherein the palladium-complexing agent is in the form of a complex with the palladium-based catalyst.

11. The process of claim 1 wherein the palladium-complexing agent contains phosphorus, and wherein the ratio of gram-atoms of phosphorus to gram-atoms of metallic palladium (or moles of palladium salt or palladium complex) ranges from 2 to 10,000.

12. The process of claim 1 wherein the tertiary nitrogen-containing organic base is triethylamine.

13. The process of claim 1 wherein the reaction temperature is between 100 and 250° C.

14. The process of claim 1 wherein the partial pressure of carbon monoxide is less than 5 bar.

15. The process of claim 14 wherein the partial pressure of carbon monoxide is about 3 bar.

16. The process of claim 5 wherein said water-immiscible organic solvent is methyl benzoate.

17. The process of claim 1 wherein said catalyst can be recycled.

* * * * *

UNITED STATES PATENT AND TRADEMARK OFFICE
CERTIFICATE OF CORRECTION

PATENT NO. : 4,990,657
DATED : February 05, 1991
INVENTOR(S) : Norbert Bluthe et al.

It is certified that error appears in the above-identified patent and that said Letters Patent is hereby corrected as shown below:

Claim 2, column 10, line 29, change "Rhd 1" to --$R_1$--.

Claim 9, column 10, line 61, change "or" (second occurrence) to --of--.

Signed and Sealed this

Ninth Day of March, 1993

Attest:

STEPHEN G. KUNIN

Attesting Officer

Acting Commissioner of Patents and Trademarks